United States Patent [19]

Hansen

[11] Patent Number: 5,387,582
[45] Date of Patent: Feb. 7, 1995

[54] VITAMIN D ANALOGUES

[75] Inventor: Kai Hansen, Herlev, Denmark

[73] Assignee: Leo Pharmaceutical Products Ltd. A/S (Lovens Kemiske Fabrik Produktionsaktiesel SKAB), Ballerup, Denmark

[21] Appl. No.: 838,795

[22] PCT Filed: Dec. 10, 1990

[86] PCT No.: PCT/DK90/00323
§ 371 Date: Mar. 17, 1992
§ 102(e) Date: Mar. 17, 1992

[87] PCT Pub. No.: WO91/09841
PCT Pub. Date: Jul. 11, 1991

[30] Foreign Application Priority Data

Dec. 22, 1989 [GB] United Kingdom ............... 8929059

[51] Int. Cl.$^6$ ............................................. C07C 401/00
[52] U.S. Cl. ........................................ 514/167; 552/653
[58] Field of Search ......................... 552/653; 514/167

[56] References Cited

FOREIGN PATENT DOCUMENTS 184112 6/1986 European Pat. Off. .

Primary Examiner—Johann Richter
Assistant Examiner—Kimberly J. Kestler
Attorney, Agent, or Firm—Cushman, Darby & Cushman

[57] ABSTRACT

The present invention relates to compounds of formula (I)

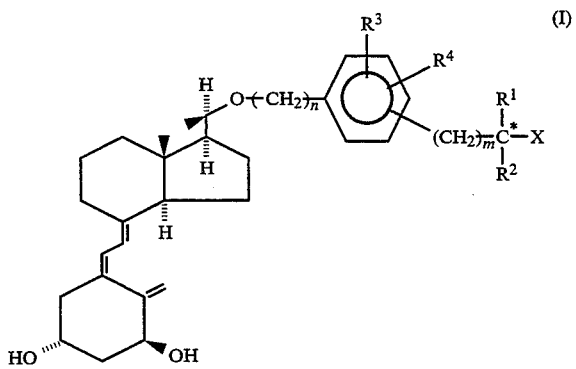

in which $R^1$ and $R^2$ may be the same or different and stand for hydrogen, lower alkyl, lower cycloalkyl, or, taken together with the carbon atom (starred in formula I), bearing the groups X, $R^1$ and $R^2$, can form a $C_3$-$C_8$ carbocyclic ring; X stands for hydrogen or hydroxy, $R^3$ and $R^4$, which may be the same or different stand for hydrogen, lower alkyl or halogen, n is 0, 1 or 2 and m is 0, 1 or 2. The present compounds, which find use both in the human and veterinary practice, show an immunomodulating effect as well as strong activity in inducing differentiation and inhibiting undesirable proliferation of certain cells, including cancer cells and skin cells.

7 Claims, No Drawings

VITAMIN D ANALOGUES

This invention relates to a hitherto unknown class of compounds which shows an immunomodulating effect as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of autoimmune diseases, including diabetes mellitus, hypertension, inflammatory diseases such as rheumatoid arthritis and asthma as well as diseases characterized by abnormal cell differentiation and/or cell proliferation, and/or imbalance in the immune system.

The compounds of the present invention are represented by the general formula I

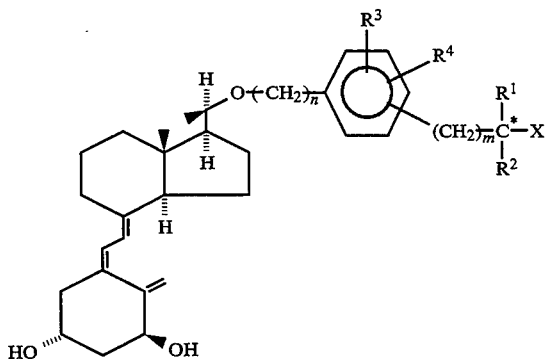

in which $R^1$ and $R^2$ may be the same or different and stand for hydrogen, lower alkyl, lower cycloalkyl, or, taken together with the carbon atom (starred in formula I), bearing the groups X, $R^1$ and $R^2$ can form a $C_3$–$C_8$ carbocyclic ring; X stands for hydrogen or hydroxy, $R^3$ and $R^4$, which may be the same or different stand for hydrogen, lower alkyl or halogen, n is 0, 1 or 2 and m is 0, 1 or 2.

In the context of this invention, the expression "lower alkyl" indicates a straight or branched saturated or unsaturated carbon chain containing from 1 to 5 carbon atoms, and the expression "lower cyclo-alkyl" indicates a saturated or unsaturated $C_3$–$C_7$ carbocyclic ring.

As can be seen from formula I, depending on the meanings of X, $R^1$ and $R^2$ the compounds of the invention can comprise several diastereoisomeric forms (e.g. R or S configuration at the starred carbon atom). The invention covers all these diastereoisomers in pure form and also mixtures of diastereoisomers. In addition, derivatives of I in which one or more of the hydroxy groups are masked as groups which can be reconverted to hydroxy groups in vivo are also within the scope of the invention ("bioreversible derivatives or prodrugs of I").

The term "bioreversible derivatives or prodrugs of I" includes, but is not limited to, derivatives of the compounds of formula I in which one or more hydroxy groups have been transformed into —O—acyl or —O—glycosyl groups, or a phosphate ester, such masked groups being hydrolyzable in vivo.

Compounds of formula I in which X is hydrogen are another type of prodrug. These compounds are relatively inactive in vitro, but are converted to active compounds of formula I (X =OH) by enzymatic hydroxylation after administration to the patient.

It has recently been shown that $1\alpha$,25-dihydroxyvitamin $D_3$ ($1,25(OH)_2D_3$) influences the effects and/or production of interleukins, indicating the potential use of this compound in the treatment of diseases characterized by a dysfunction of the immune system, e.g. autoimmune diseases and rejection of transplants. In addition, other conditions characterized by an abnormal interleukin-1 production, e.g. inflammatory diseases such as rheumatoid arthritis may be treated with $1,25(OH)_2D_3$.

It has also been shown that $1,25(OH)_2D_3$ is able to stimulate the differentiation of cells and inhibit excessive cell proliferation, and it has been suggested that this compound might be useful in the treatment of diseases characterized by abnormal cell proliferation and/or cell differentiation such as cancer and psoriasis.

Also, the use of $1,25(OH)_2D_3$ for the treatment of hypertension and diabetes mellitus has been suggested.

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and its potent synthetic analogues are not completely satisfatory for use as drugs in the treatment of e.g. psoriasis, cancer or immune diseases which may require continuous administration of the drug in relatively high doses.

A number of oxa-analogues of vitamin $D_3$ are known. $1\alpha$,25-dihydroxy-20-oxa-21-norvitamin $D_3$ and $1\alpha$-hydroxy-20-oxa-21-norvitamin $D_3$ are described in N. Kubodera et al, Chem. Pharm. Bull., 34, 2286 (1986), $1\alpha$,25-dihydroxy-22-oxavitamin $D_3$ and 25-hydroxy-22-oxavitamin $D_3$ are described in E. Murayama et al, Chem. Pharm. Bull., 34, 4410 (1986), J. Abe et al, FEBS LETTER, 226, 58 (1987) and European Patent Application, publication number 184 112, $1\alpha$,25-dihydroxy-23-oxavitamin $D_3$ is described in European Patent Application, publication number 78704, and a number of 22-oxa-analogues of vitamin $D_3$ are described in International Patent Applications Nos PCT/DK90/00037 and PCT/DK90/00036, both filed on Feb. 13, 1990.

In vitro experiments indicate that some of these compounds may have advantages over $1,25(OH)_2D_3$. Thus $1\alpha$,25-dihydroxy-22-oxavitamin $D_3$ has only one 14th as much affinity as $1\alpha$,25$(OH)_2D_3$ for the chick intestinal cytosolic receptor, a weaker affinity than $1,25(OH)_2D_3$ for the receptor in a human myeloid leukemia cell line (HL-60), and a high activity as inducer of differentiation in HL-60 cells.

In contrast to the compounds of the present invention the above mentioned 22-oxa-compounds do not contain an aromatic ring.

The usefulness of a vitamin D analogue in the above mentioned indications is dependent not only upon a favourable ratio of binding affinity to relevant receptors compared to the intestinal receptor, but also upon the fate of the compound in the organism.

It has now been found that the compounds of the present invention show favourable selectivity with respect to receptor binding and at the same time show high bioavailability as well as chemical and metabolic stability.

The selectivity of the compounds is illustrated by the fact that while they have high affinities for the receptor in tumour cells (similar to or much better than that of $1,25(OH)_2D_3$) and the concentration needed to induce cell differentiation in a human monocytic tumour cell line is the same as or considerably lower than that needed of 1,25(OH)$_2$D$_3$ to give the same effect, their binding affinity for the intestinal receptor is lower than that of 1,25(OH)$_2$D$_3$. In vivo in rats the compounds are less active than 1,25(OH)$_2$D$_3$ in inducing hypercalciuria and hypercalcemia.

This renders the compounds of the invention especially suited for both local and systemic treatment and prophylaxis of human and veterinary disorders which are characterized by abnormal cell proliferation and/or cell differentiation, such as certain dermatological disorders including psoriasis and acne, and certain cancer forms, e.g. leukemia and myelofibrosis, and diseases characterized by an imbalance in the immune system, e.g autoimmune diseases or AIDS, and to obtain desired immunosuppression as in transplantation procedures, as well as treatment of diabetes mellitus and hypertension and inflammatory diseases, such as rheumatoid arthritis and asthma. As the compounds of this invention may promote the differentiation of the hair follicle cells, these compounds may be used in the treatment of alopecia. Preliminary studies indicate that the compounds of the invention may reverse the unattractive concomitants of skin ageing, e.g. on photoaged skin.

The compounds of formula I may conveniently be prepared from the vitamin D-derivative 1 (or its 20R isomer) (Tetrahedron, 43, 4609 (1987)) by the routes outlined in Scheme 1. Oxidation of 1 for example using the van Rheenen procedure (Tetrahedron Letters, 1969, 985) gives the ketone 2, which is reduced to the 20R-alcohol 3. When a suitable chiral reducing agent is used 3 may be prepared with very high stereoselectivity, but 3 is conveniently prepared by NaBH$_4$ reduction of 2 and separating the minor amount of corresponding 20S-alcohol chromatographically. O-Alkylation of 3 to give III is achieved by treatment under basic conditions with a side chain building block of general formula Z-R, in which Z is a leaving group such as a halogen (Cl, Br or I) or p-toluenesulphonyloxy or methanesulphonyloxy, and R is as defined in the notes to Scheme 1. Thus R in compounds III, IV, V and VI does not necessarily have the same meaning along a particular synthetic sequence, and the conversion of R to the side chain in I may well involve several steps. Apart from any necessary modification within the side chain (R), the conversion of III to I involves a photoisomerisation step and a desilylation step, analogous to the steps used in the last stages of the synthesis of other vitamin D analogues (see European patent No. 0 227 826).

The side chain building blocks, RZ, are either known compounds or may be prepared analogously to those described in PCT/DK89/00079. They may typically be prepared by the routes outlined in Scheme 2.

The following standard abbreviations are used throughout this disclosure: Me=methyl; Et=ethyl; Pr$^n$=n-propyl; Pr$^i$=isopropyl; Bu$^t$=tert-butyl; THP=tetra-hydro-4H-pyran-2-yl; THF=tetrahydrofuran; Ts=p-toluenesulphonyl; TBA=tetra-(n-butyl)-ammonium.

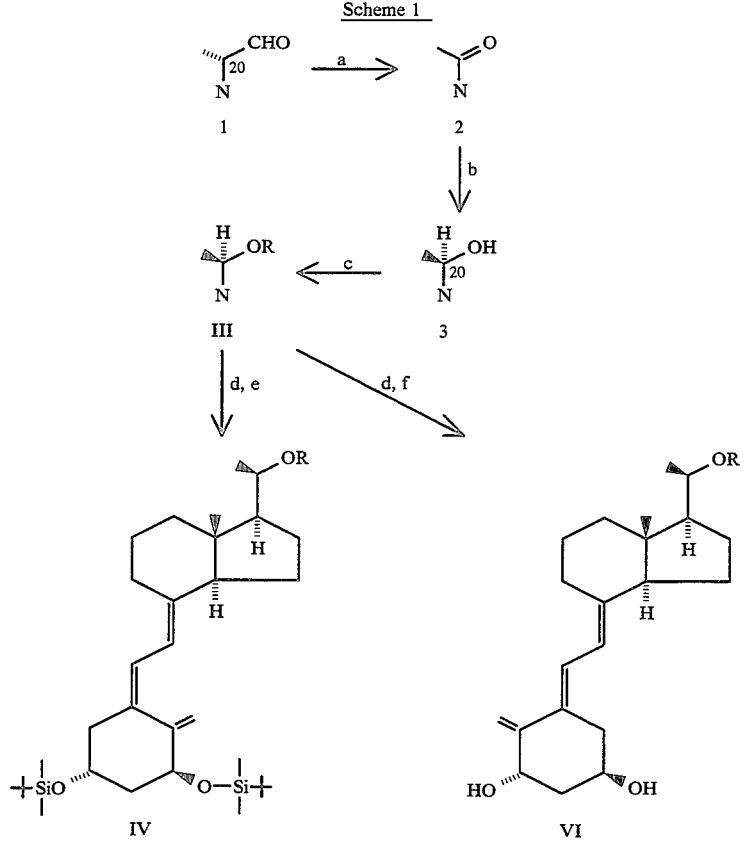

Scheme 1

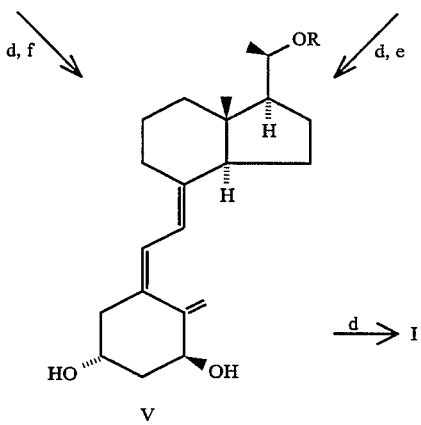

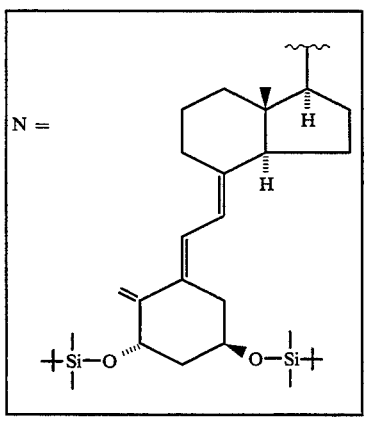

Notes to Scheme 1

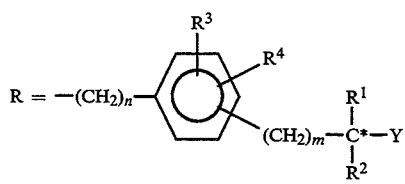

where Y is hydrogen or hydroxyl in which the hydroxyl group may optionally be protected by a protective groups, such as trialkylsilyl or THP. n, m, $R^1$, $R^2$, $R^3$, and $R^4$ are as defined as above.

a) Oxidation e.g. with $O_2$ with $Cu(AcO)_2$, 2,2'-bipyridyl and 1,4-diazabicyclo[2,2,2]octane as catalyst.
b) Reduction (e.g. with $NaBH_4$).
c) Alkylation with the side chain fragment R-Z in the presence of base (e.g. KOH, KOBu$^t$ or KH, with or without catalyst (e.g. 18-Crown-6) in solvent, e.g. THF.
d) Optional functional group modification in the side chain.
e) Isomerisation with hν - triplet sensitizer, e.g. anthracene.
f) Deprotection with $TBA^+F^-$ or HF.

It should be noted that although the shown intermediates may have hydroxyl groups protected as tert-butyldimethylsilyl ethers, the scope of the invention does not exclude the use of alternative hydroxyl protecting groups well known in the art (such as those described in T. W. Greene, "Protective groups in organic synthesis", Wiley, New York, 1981), together with alternative reactions for deprotection.

Scheme 2
Examples of Routes for the Preparation of the Side Chain Fragment R—Z

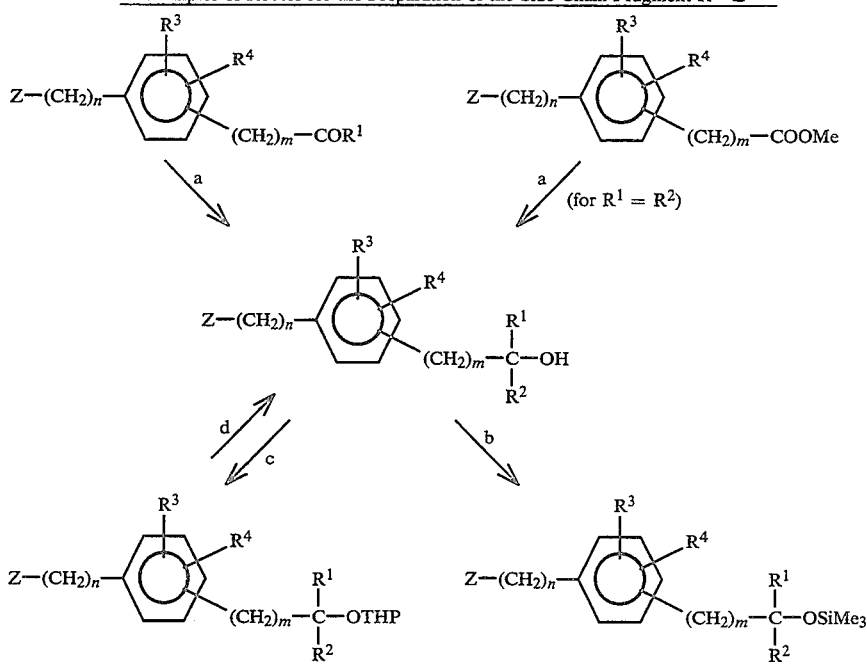

Notes to Scheme 2
a) Grignard reaction with $R^2MgBr$ or $R^2MgI$
b) Silylation with $Me_3SiCl$ + base
c) Reaction with dihydropyran
d) Acid hydrolysis The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis, topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye formulations, include liquid or semi-liquid preparations such as liniments, lotions, applicants, oil-in-water or water-in-oil emulsions such as creams, ointments, including eye ointments, pastes; or solutions or suspensions such as drops, including eye-drops.

For asthma treatment inhalation of powder, self-propelling or spray formulations, dispensed with a spray can, a nebulizer or an atomizer can be used. The formulations, when dispensed, preferably have a particle size in the range of 10 to 100μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and flourinated $C_1$-$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1-100 μg, preferably from 0.2-25 μg, of a compound of formula I are administered. In the topical treatment of dermatological disorders, ointments, creams or lotions containing from 1-1000 μg/g, and preferably from 10-500 μg/g, of a compound of formula I are administered. The oral compositions are formulated, preferably as tablets, capsules, or drops, containing from 0.1-50 μg, preferably from 0.2-25 μg, of a compound of formula I, per dosage unit.

The invention will now be further described in the following non-limiting Preparations and Examples:

PREPARATIONS AND EXAMPLES

General

The exemplified compounds I are listed in Table 1. The intermediates of Scheme I referred to in the Preparations are to be identified by numbers with the corresponding formulae in Table 2.

For nuclear magnetic resonance spectra (300 MHz) chemical shift values (δ) are quoted for deuteriochloroform solutions relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue.

TABLE 1

Exemplified Compounds I

Position of the group:
$$-(CH_2)_m-\overset{R^1}{\underset{R^2}{C^*}}-X$$

| Compound No. | Example No. | n | m | $R^1$ | $R^2$ | $R^3$ | $R^4$ | X | |
|---|---|---|---|---|---|---|---|---|---|
| 101 | 1 | 1 | 0 | Me | Me | H | H | OH | 3 |
| 102 | 2 | 1 | 0 | Me | Me | H | H | OH | 4 |

TABLE 1-continued

Exemplified Compounds I

Position of the group:
$$-(CH_2)_m-\overset{R^1}{\underset{R^2}{C^*}}-X$$

| Compound No. | Example No. | n | m | $R^1$ | $R^2$ | $R^3$ | $R^4$ | X | Position |
| --- | --- | --- | --- | --- | --- | --- | --- | --- | --- |
| 103 | 3 | 1 | 0 | Et | Et | H | H | OH | 3 |
| 104 | 4 | 1 | 1 | Me | Me | H | H | OH | 2 |
| 105 | 5 | 1 | 0 | Me | Me | 6-Me | H | OH | 3 |
| 106 | 6 | 2 | 0 | $Pr^n$ | $Pr^n$ | H | H | OH | 2 |
| 107 | 7 | 1 | 0 | Me | Me | 2-F | H | OH | 4 |

TABLE 2

Preparations of formula III or IV
(See Scheme 1)

Position of the group:
$$-(CH_2)_m-\overset{R^1}{\underset{R^2}{C^*}}-Y$$

| Compound No. | Preparation No. | Type (Scheme 1) | n | m | $R^1$ | $R^2$ | $R^3$ | $R^4$ | Y | Position |
| --- | --- | --- | --- | --- | --- | --- | --- | --- | --- | --- |
| 4 | 4 | III | 1 | 0 | Me | Me | H | H | O-THP | 3 |
| 5 | 5 | IV | 1 | 0 | Me | Me | H | H | O-THP | 3 |
| 6 | 7 | III | 1 | 0 | Me | Me | H | H | O-THP | 4 |
| 7 | 8 | IV | 1 | 0 | Me | Me | H | H | O-THP | 4 |
| 8 | 10 | III | 1 | 0 | Et | Et | H | H | O-THP | 3 |
| 9 | 11 | IV | 1 | 0 | Et | Et | H | H | O-THP | 3 |
| 10 | 13 | III | 1 | 1 | Me | Me | H | H | O-THP | 2 |
| 11 | 14 | IV | 1 | 1 | Me | Me | H | H | O-THP | 2 |
| 12 | 16 | III | 1 | 0 | Me | Me | 6-Me | H | O-THP | 3 |
| 13 | 17 | IV | 1 | 0 | Me | Me | 6-Me | H | O-THP | 3 |
| 14 | 19 | III | 2 | 0 | $Pr^n$ | $Pr^n$ | H | H | O-THP | 2 |
| 15 | 20 | IV | 2 | 0 | $Pr^n$ | $Pr^n$ | H | H | O-THP | 2 |
| 16 | 23 | III | 1 | 0 | Me | Me | 2-F | H | O-THP | 4 |
| 17 | 24 | IV | 1 | 0 | Me | Me | 2-F | H | O-THP | 4 |

Preparation 1: Compound 2

To a solution of 1(S),3(R)-bis-(tert-butyldimethyl-silyloxy)-20(S)-formyl-9,10-secopregna-5(E),-(7E),10(19)-triene (3.44 g, 6 mmol) in N,N-dimethylformamide (150 ml), 1,4-diazabicyclo[2.2.2]octane (600 mg, 5.3 mmol), cupric acetate, monohydrate (90 mg, 0.45 mmol) and 2,2'-bipyridyl (72 mg, 0.45 mmol) were added. Air was bubbled through the well stirred solution for 6 days at 40° C.

The reaction mixture was diluted with ethyl acetate (500 ml), extracted with water (2×100 ml) and saturated aqueous sodium chloride (3×50 ml) and dried over MgSO$_4$. Ethyl acetate was evaporated off, and the solid residue was purified by chromatography (silica gel, 10% ether in petroleum ether as eluant) to give the title compound.

NMR: δ=0.037 (s, 3H), 0.043 (s, 3H), 0.056 (s, 6H), 0.49 (s, 3H), 0.84 (s, 9H), 0.89 (s, 9H), 1.5–2.30 (m, 13H), 2.13 (s, 3H), 2.55 (dd, 1H), 2.70 (t, 1H), 2.89 (bd, 1H), 4.21 (m, 1H), 4.52 (m, 1H), 4.94 (m, 1H), 4.98 (m, 1H), 5.83 (d, 1H), 6.43 (d, 1H) ppm.

Preparation 2: Compound 3 and its 20S-isomer

Compound 2 (Prep. 1) (3.10 g, 5.5 mmol) was dissolved in tetrahydrofuran (140 ml) and sodium borohydride (0.35 g, 3.3 mmol) was added. Methanol (100 ml) was then added dropwise over 15 minutes. The reaction blend was stirred for 20 minutes, then diluted with ethyl acetate (560 ml). The solution was extracted with water (5×150 ml) and saturated aqueous sodium chloride (150 ml), dried over MgSO$_4$ and evaporated to give a colourless oil. The oily residue was purified by chromatography (silica gel, 15% ethyl acetate in petroleum ether as eluant). The first eluted isomer (3A) was dissolved in methanol (3 ml). Upon scratching a crystalline product precipitated. The suspension was stirred for 1 h at room temperature and 1 h in an ice bath. The crystals were collected on a filter and dried in a desiccator over the week-end.

Mp. 131°–146° C.

NMR: δ=0.05 (m, 12H), 0.62 (s, 3H), 0.86 (s, 9H), 0.89 (s, 9H), 1.10–2.10 (m, 14H), 1.15 (d, 3H), 2.30 (bd, 1H), 2.53 (dd, 1H), 2.89 (m, 1H), 2.89 (m, 1H), 3.71 (m, 1H), 4.21 (m, 1H), 4.52 (m, 1H), 4.93 (m, 1H), 4.98 (m, 1H), 5.81 (d, 1H), 6.45 (d, 1H) ppm.

The fractions containing the more polar 20S-isomer were evaporated to give a colourless residue.

NMR: δ=0.052 (bd, 12H), 0.54 (s, 3H), 0.85 (s, 9H), 0.89 (s, 9H), 1.22 (d, 3H), 1.20–2.10 (m, 14H), 2.30 (bd, 1H), 2.55 (dd, 1H), 2.87 (m, 1H), 3.72 (m, 1H), 4.21 (m, 1H), 4.52 (m, 1H), 4.94 (bs, 1H), 4.98 (m, 1H), 5.82 (d, 1H ), 6.44 ( d, 1H ) ppm.

A sample of the residue was dissolved in methanol. Upon scratching a crystalline product was formed. The suspension was placed in the refrigerator over the week-end. The crystals were collected on a filter and dried in a desiccator.

M.p. 58°–63° C.

Preparation 3: 2-[2-(3-Bromomethylphenyl)-2-propyl-oxy]-tetrahydro-4H-pyran

To a stirred, ice-cooled solution of methyl 3-bromomethyl-benzoate (6.12 g, 27 mmol) in dried ether (20 ml) was added dropwise over 30 minutes a filtered solution of a Grignard reagent, prepared from magnesium (1.47 g, 60 mmol) and methyl iodide (4.0 ml, 64 mmol) in dried ether (40 ml). After a further 20 minutes in the ice-bath, water (40 ml) was slowly poured onto the reaction mixture. The phases were separated, and the aqueous phase was extracted with ether (3×50 ml). The combined ether phases were consecutively extracted with water (3×50 ml) and saturated aqueous sodium chloride (50 ml), dried with MgSO$_4$ and concentrated in vacuo to yield a dark oil.

The crude oil was then purified by chromatography (silica gel, 25% ether in petroleum ether as eluant) to yield the intermediate 2-(3-bromomethylphenyl)-propan-2-ol as a yellow oil.

The intermediate was dissolved in methylene chloride (100 ml), 3,4-dihydro-2H-pyran (2.4 ml, 26 mmol) and pyridinium p-toluene sulfonate (0.43 g, 1.7 mmol) were added, and the mixture was stirred at room temperature for 4 hours. The reaction mixture was diluted with ether (150 ml) and extracted with water (3×50 ml) and saturated aqueous sodium chloride (50 ml), dried and concentrated in vacuo. The product was then purified by chromatography (silica gel, 10% ether in petroleum ether as eluant) to give a colourless oil.

NMR: $\delta$=1.52 (s, 3H), 1.67 (s, 3H), 1.35–1.75 (m, 5H), 1.85 (m, 1H), 3.39 (m, 1H), 3.95 (m, 1H), 4.43 (dd, 1H), 4.51 (AB quartet, 2H), 7.28 (m, 2H), 7.38 (m, 1H), 7.49 (m, 1H) ppm.

Preparation 4: Compound 4
(R=3-[2-(tetrahydro-4H-pyran-2-yl)-oxy-propyl-2]-phenyl-methyl)

To a solution of compound 3 (841 mg, 1.5 mmol) in dry tetrahydrofuran (10 ml), potassium hydride (1.0 ml, 20% suspension in oil) and 2-[2-(3-bromomethylphenyl)-2-propyl]tetrahydro-4H-pyran (2.01 ml), 6.75 mmol) were added, and the reaction mixture stirred vigorously. 18-Crown-6 (650 mg, 5.8 mmol) was dissolved in dry tetrahydrofuran (5 ml) and added dropwise over 20 minutes. After a further 90 minutes stirring, water (40 ml) was carefully added to the reaction mixture. After the reaction had subsided, the reaction mixture was diluted with ether (100 ml), and the organic phase consecutively extracted with water (3×50 ml) and aqueous saturated sodium chloride (50 ml). After drying and the removal of the solvent in vacuo, the product was purified by chromatography (silica gel, 10% ether in petroleum ether as eluant) to give the desired compound as a colourless oil.

NMR: $\delta$=0.06 (bs, 12H), 0.52 and 0.54 (2s, 3H), 0.85 (s, 9H), 0.89 (s, 9H), 1.17 (d, 3H), 1.49 (bs, 3H), 1.65 (bs, 3H), 1.10–1.98 (m, 17H), 2.04 (m, 1H), 2.22(m, 1H), 2.31 (bd, 1H), 2.54 (dd, 1H), 2.86 (bd, 1H), 3.37 (m, 1H), 3.45 (m, 1H), 3.94 (m, 1H), 4.21 (m, 1H), 4.34 (d, J=11.3, 1H), 4.39 (m, 1H), 4.53 (m, 1H), 4.60 (d, J=11.3, 1H), 4.93 (m, 1H), 4.98 (m, 1H), 5.80 (d, J=11.4, 1H), 6.45 (d, J=11.4, 1H), 7.20 (bd, 1H), 7.28 (t, 1H), 7,36 (bd, 1H), 7.44 (bs, 1H) ppm.

Preparation 5: Compound 5
(R=3-[2-(tetrahydro-4H-pyran-2-yl)-oxy-propyl-2]-phenyl-methyl)

A solution of compound 4 (Prep. 4) (800 mg, 1.0 mmol ), anthracene (800 mg, 4.5 mmol) and triethylamine (1 drop) in dichloromethane (60 ml ) under nitrogen in a Pyrex flask was irradiated with light from a high pressure ultra-violet lamp, type TQ 718-Z2 (Hanau), at room temperature for 35 minutes. The solution was filtered and concentrated in vacuo. The residue was purified by chromatography (silica gel, 10% ether in petroleum ether as eluant) to give the desired compound as a colourless oil.

NMR: $\delta$=0.05 (bs, 12H), 0.50 and 0.53 (2s, 3H), 0.87 (s, 18H), 1.16 (d, 3H), 1.48 (bs, 3H), 1.65 (bs, 3H), 1.10–1.93 (m, 17H), 2.00 (t, 1H), 2.20 (m, 2H), 2.44 (m, 1H), 2.81 (bd, 1H), 3.38 (m, 1H), 3.45 (m, 1H), 3.95 (m, 1H), 4.18 (m, 1H), 4.34 (d, J=11.4, 1H), 4.40 (m, 2H), 4.59 (d, J=11.4, 1H), 4.85 (m, 1H), 5.16 (m, 1H), 5.99 (d, J=11.1, 1H), 6.23 (d, J=11.1, 1H), 7.19 (bd, 1H), 7.28 (t, 1H), 7,36 (bd, 1H), 7.44 (bd, 1H) ppm.

Preparation 6:
2-[2-(4-Bromomethylphenyl)-2-propyl-oxy]-tetrahydro-4H-pyran

By following the procedure of Preparation 3 and substituting methyl 4-bromomethyl-benzoate for methyl 3-bromomethyl-benzoate, the title compounds was prepared.

NMR: $\delta$=1.50 (s, 3H), 1.66 (s, 3H), 1.35–1.70 (m, 5H), 1.85 (m, 1H), 3.40 (m, 1H), 3.95 (m, 1H), 4.44 (m, 1H), 4.50 (s, 2H), 7.37 (m, 4H).

Preparation 7: Compound 6 (
R=4-[2-(tetrahydro-4H-pyran-2-yl)-oxy-propyl-2]-phenyl-methyl)

This compound was prepared by following the procedure of Preparation 4 and substituting 2-[2-(4-bromomethylphenyl) -2-propyl]-tetrahydro-4H-pyran for 2-[2-(3-bromomethylphenyl) -2-propyl]-tetrahydro-4H-pyran.

NMR: $\delta$=0.06 (bs, 12H), 0.52 and 0.53 (2s, 3H), 0.86 (s, 9H), 0.89 (s, 9H), 1.17 (d, 3H), 1.49 (bs, 3H), 1.66 (bs, 3H), 1.10–1.97 (m, 17H), 2.05 (m, 1H), 2.16 (m, 1H), 2.31 (bd, 1H), 2.54 (dd, 1H), 2.87 (bd, 1H), 3.37 (m, 1H), 3.45 (m, 1H), 3.95 (m, 1H), 4.21 (m, 1H), 4.36 (d, J=11.2, 1H), 4.40 (m, 1H), 4.52 (m, 1H), 4.57 d, J=11.2, 1H), 4.93 (m, 1H), 4.98 (m, 1H), 5.80 (d, J=11.4, 1H), 6.46 (d, J=11.4, 1H), 7.30 (d, 2H), 7.40 (bs, 2H) ppm.

Preparation 8: Compound 7
(R=3-[2-(tetrahydro-4H-pyran-2-yl)-oxy-propyl-2]-phenyl-methyl)

This compound was prepared by following the procedure of Preparation 5 and substituting compound 5 (Prep. 7) for compound 5 (Prep. 4).

NMR: $\delta$=0.06 (bs, 12H), 0.50 and 0.52 (2s, 3H), 0.87 (bs, 18H), 1.16 (d, 3H), 1.49 (bs, 3H), 1.66 (bs, 3H), 1.00–1.92 (m, 17H), 2.00 (bt, 1H), 2.20 (m, 2H), 2,45 (dd, 1H), 2.82 (bd, 1H), 3.40 (m, 2H), 3.95 (m, 1H), 4.18 (m, 1H), 4.37 (m, 1H), 4.56 (d, J=11.3, 1H), 4.86 (m, 1H), 5.17 (m, 1H), 5.99 (d, J=11.0, 1H), 6.23 (d, J=11.0, 1H), 7.30 (d, 2H), 7.41 (d, 2H) ppm.

Preparation 9:
2-[3-(3-Bromomethylphenyl)-3-pentyl-oxy]-tetrahydro-4H-pyran

The compound was prepared according to the procedure described in Preparation 3, except that methyl magnesium iodide was substituted with ethyl magnesium bromide.

NMR: $\delta$=0.63 (t, 3H), 0.77 (t, 3H), 1.42–1.75 (m, 5H), 1.77–2.15 (m, 5H), 3.43 (m, 1H), 4.00 (m, 1H), 4.52 (AB q, 2H), 4.58 (m, 1H), 7.20–7.38 (m, 3H), 7.45 (bs, 1H) ppm.

Preparation 10: Compound 8 (R=3-[3-(tetrahydro-4H-pyran-2-yl)-oxy-pentyl-3]-phenyl-methyl)

The compound was prepared according to the procedure described in Preparation 4, except that 2-[2-(3-bromomethylphenyl) -2-propyl-oxy]-tetrahydro-4H-pyran was substituted with 2-[3-(3-bromomethyl-phenyl)-3-pentyl-oxy]-tetrahydro-4H-pyran.

NMR: δ=0.06 (m, 12H), 0.53 (s, 0.5×3H), 0.54 (s, 0.5×3H), 0.59 (t, 3H), 0.76 (dt, 3H), 0.86 (s, 9H), 0.89 (s, 9H), 1.17 (d, 3H), 1.10–2.12 (m, 22H), 2.19 (bd, 1H), 2.30 (bd, 1H), 2.54 (dd, 1H), 2.85 (bd, 1H), 3.44 (m, 2H), 3.97 (m, 1H), 4.21 (m, 1H),. 4.33 (d, 1H), 4.57 (m, 3H), 4.93 (m, 1H), 4.98 (m, 1H), 5.80 (d, 1H), 6.45 (d, 1H), 7.10–7.45 (m, 4H) ppm.

Preparation 11: Compound 9 (R=3-[3-(tetrahydro-4H-pyran-2-yl)-oxy-pentyl-3]-phenyl-methyl)

The compound was prepared according to the procedure described in Preparation 5, except that the compound 4 prepared in Preparation 4 was substituted with the compound 8 prepared in Preparation 10.

NMR: δ=0.05 (m, 12H), 0.51 (s, 0.5×3H), 0.52 (s, 0.5×3H), 0.59 (t, 3H), 0.76 (dt, 3H), 0.87 (s, 18H), 1.16 (d, 3H), 1.05–2.10 (m, 22H), 2.20 (m, 2H), 2.44 (dd, 1H), 2.80 (bd, 1H), 3.43 (m, 2H), 3.97 (m, 1H), 4.18 (m, 1H), 4.32 (d, 1H), 4.36 (m, 1H), 4.56 (m, 2H), 4.85 (m, 1H), 5.17 (m, 1H), 5.98 (d, 1H), 6.23 (d, 1H), 7.18 (d, 1H), 7.27 (t, 1H), 7.34 (d, 1H), 7.39 (bd, 1H) ppm.

Preparation 12: 2-[1-(2-Chloromethylphenyl)-2-methyl-2-propyl-oxy]-tetrahydro-4H-pyran The compound is prepared according to the procedure described in Preparation 3, except that methyl 3-bromomethyl-benzoate is substituted with methyl 2-chloromethylphenylacetate.

Preparation 13: Compound 10 (R=2-[2-(tetrahydro-4H-pyran-2-yl)-oxy-2-methyl-propyl]-phenylmethyl)

The compound is prepared according to the procedure described in Preparation 4, except that 2-[2-(3-bromomethyl-phenyl)-2-propyl-oxy]-tetrahydro-4H-pyran is substituted with 2-[2-(2-chloromethylphenyl)-2-methyl-2-propyl-oxy]-tetrahydro-4H-pyran.

Preparation 14: Compound 11 (R=2-[2-(tetrahydro-4H-pyran-2-yl)-oxy-2-methyl-propyl]-phenylmethyl)

The compound is prepared according to the procedure described in Preparation 5, except that the compound 4 prepared in Preparation 4 is substituted with the compound 10 prepared in Preparation 13.

Preparation 15: 2-[2-(3-Chloromethyl-4-methyl-phenyl)-2-propyl-oxy]-tetrahydro-4H-pyran The compound is prepared according to the procedure described in Preparation 3, except that methyl 3-bromomethyl-benzoate is substituted with methyl 3-chloromethyl-4-methyl-benzoate.

Preparation 16: Compound 12 (R=3-[2-(tetrahydro-4H-pyran-2-yl)-oxy-propyl-2]-6-methyl-phenylmethyl)

The compound is prepared according to the procedure described in Preparation 4, except that 2-[2-(3-bromomethylphenyl)-2-propyl-oxy]-tetrahydro-4H-pyran is substituted with 2-[2-(3-chloromethyl-4-methyl-phenyl)-2-propyl-oxy]-tetrahydro-4H-pyran.

Preparation 17: Compound 13 (R=3-[2-(tetrahydro-4H-pyran-2-yl)-oxy-propyl-2]-6-methylphenylmethyl)

The compound is prepared according to the procedure described in Preparation 5, except that the compound 4 prepared in Preparation 4 is substituted with the compound 12 prepared in Preparation 16.

Preparation 18: 2-[4-(2-(2-bromoethyl)-phenyl)-4-heptyl-oxy]-tetrahydro-4H-pyran The compound is prepared according to the procedure described in Preparation 3, except that methyl 3-bromo-methyl-benzoate is substituted with methyl 2-(2-bromoethyl)-benzoate and methyl magnesium iodide is substituted with n-propyl magnesium bromide.

Preparation 19: Compound 14 (R=2-[2-[4-tetrahydro-4H-pyran-2-yl)-oxy-4-heptyl]-phenyl)-ethyl The compound is prepared according to the procedure described in Preparation 4, except that 2-[2-(3-bromomethylphenyl)-2-propyl-oxy]-tetrahydro-4H-pyran is substituted with 2-[2-(2-bromoethyl)-phenyl)-4-heptyl-oxy]-tetrahydro-4H-pyran.

Preparation 20: Compound 15 (R=2-(2-[4-tetrahydro-4H-pyran-2-yl)-oxy-4-heptyl]-phenyl)-ethyl The compound is prepared according to the procedure described in Preparation 5, except that the compound 4 prepared in Preparation 4 is substituted with the compound 14 prepared in Preparation 19.

Preparation 21: Methyl 2-(2-bromoethyl)-benzoate 2-(2-Bromoethyl)-benzoic acid (11.4 g, 50 mmol) is added to a solution of diazomethan in ether at 0° C. The reaction mixture is concentrated in vacuo, and the residue purified by chromatography to give the desired compound as a colourless oil.

Preparation 22: 2-[2-(4-Bromomethyl-3-fluoro-phenyl)-2-propyl-oxy]-tetrahydro-4H-pyran The compound is prepared according to the procedure described in Preparation 3, except that methyl 3-bromomethyl-benzoate is substituted with ethyl 4-bromomethyl-3-fluoro-benzoate.

Preparation 23: Compound 16 (R=4-[2-(tetrahydro-4H-pyran-2-yl)-oxy-propyl-2]-2-fluoro-phenylmethyl The compound is prepared according to the procedure described in Preparation 4, except that 2-[2-(3-bromomethylphenyl)-2-propyl-oxy]-tetrahydro-4H-pyran is substituted with 2-[2-(4-bromomethyl-3-fluoro-phenyl)-2-propyl-oxy]-tetrahydro-4H-pyran.

Preparation 24: Compound 17
(R=4-[2-(tetrahydro-4H-pyran-2-yl)-oxy-propyl-2]-2-fluoro-phenylmethyl The compound is prepared according to the procedure described in Preparation 5, except that the compound 4 prepared in Preparation 4 is substituted with the compound 16 prepared in Preparation 23.

Example 1
1(S),3(R)-Dihydroxy-20(R)-(3-(2-hydroxy-2-propyl)-phenylmethyloxy)-9,10-seco-pregna-5(Z),7(E),10(19)-triene (Compound 101

The compound prepared in Preparation 5 (700 mg, 0.88 mmol) was dissolved in ethyl acetate (1.0 ml). Acetonitrile (24 ml) was added under vigorous stirring. A solution of 5% hydrofluoric acid in acetonitrile/water 8:1 (10.6 ml) was added, and the reaction mixture stirred under nitrogen at room temperature for 45 minutes. Ethyl acetate (150 ml) was added, and the reation mixture consecutively extracted with saturated aqueous sodium hydrogen carbonate (60 ml), water (3×60 ml) and saturated aqueous sodium chloride (50 ml), dried with magnesium sulphate and concentrated in vacuo. The residue was purified by chromatography (silica gel, 20% pentane in ethyl acetate as eluant) to give the title compound.

NMR: $\delta$=0.54 (s, 3H), 1.18 (d, 3H), 1.57 (s, 6H), 1.12–2.06 (m, 15H), 2.22 (bd, 1H), 2.30 (dd, 1H), 2.59 (dd, 1H), 2.82 (m, 1H), 3.45 (m, 1H), 4.22 (bm, 1H), 4.35 (d, J=11.3, 1H), 4.42 (bm, 1H), 4.61 (d, J=11.3, 1H), 4.99 (m, 1H), 5.32 (m, 1H), 5.99 (d, J=11.3, 1H), 6.38 (d, J=11.3, 1H), 7.20 (bd, 1H), 7.30 (t, 1H), 7.40 (bd, 1H), 7.50 (bd, 1H), ppm.

Example 2
1(S),3(R)-Dihydroxy-20(R)-(4-(2-hydroxy-2-propyl)-phenylmethyloxy)-9,10-seco-pregna-5(Z),7(E),10(19)-triene (Compound 102)

This compound was prepared by following the procedure of Example 1 and substituting the compound prepared in Preparation 8 for the compound prepared in Preparation 5.

NMR: $\delta$=0.54 (s, 3H), 1.16 (d, 3H), 1.58 (s, 6H), 1.10–2.10 (m, 15H), 2.17 (m, 1H), 2.32 (dd, 1H), 2.60 (m, 1H), 2.83 (m, 1H), 3.43 (m, 1H), 4.23 (m, 1H), 4.35 (d, J=11.3, 1H), 4.43 (m, 1H), 4.57 (d, J=11.3, 1H), 5.00 (m, 1H), 5.32 (m, 1H), 6.00 (d, J=11.2, 1H), 6.39 (d, J=11.2, 1H), 7.32 (d, 2H), 7.45 (d, 2H) ppm.

Example 3
1(S),3(R)-Dihydroxy-20(R)-(3-(3-hydroxy-3-pentyl)-phenylmethyloxy)-9,10-seco-pregna-5(Z),7(E),10(19)-triene (Compound 103)

This compound was prepared by following the procedure of Example 1 and substituting the compound 9 prepared in Preparation 11 for the compound 5 prepared in Preparation 5.

NMR: $\delta$=0.54 (s, 3H), 0.74 (t, 6H), 1.17 (d, 3H), 1.10–2.10 (m, 19H), 2,19 (bd, 1H), 2.31 (dd, 1H), 2.59 (dd, 1H), 2.81 (bd, 1H), 3.45 (m, 1H), 4.22 (m, 1H), 4.33 (d, 1H), 4.42 (m, 1H), 4.62 (d, 1H), 5.00 (m, 1H), 5.32 (m, 1H), 5.99 (d, 1H), 6.38 (d, 1H), 7.18 (m, 1H), 7.27 (m, 2H), 7.38 (bs, 1H) ppm.

Example 4
1(S),3(R)-Dihydroxy-20(R)-(2-(2-hydroxy-2-methyl-propyl)-phenylmethyloxy)-9,10-seco-pregna-5(Z),7(E),-10(19)-triene (Compound 104)

This compound is prepared by following the procedure of Example 1 and substituting the compound 11 prepared in Preparation 14 for the compound 5 prepared in Preparation 5.

Example 5
1(S),3(R)-Dihydroxy-20(R)-(3-(2-hydroxy-propyl-2)-6-methyl-phenylmethyloxy)-9,10-seco-pregna-5(Z),7(E),-10(19)-triene (Compound 105)

This compound is prepared by following the procedure of Example 1 and substituting the compound 13 prepared in Preparation 17 for the compound 5 prepared in Preparation 5.

Example 6
1(S),3(R)-Dihydroxy-20(R)-(2-(2-(4-hydroxy-4-heptyl)-phenyl)-ethyloxy)-9,10-seco-pregna-5(Z),7(E),10(19)-triene (Compound 106)

This compound is prepared by following the procedure of Example 1 and substituting the compound 15 prepared in Preparation 20 for the compound 5 prepared in Preparation 5.

Example 7
1(S),3(R)-Dihydroxy-20(R)-(4-(2-hydroxy-propyl-2)-2-fluoro-phenylmethyloxy-9,10-seco-pregna-5(Z),-7(E),10(19)-triene (Compound 107)

This compound is prepared by following the procedure of Example 1 and substituting the compound 17 prepared in Preparation 24 for the compound 5 prepared in Preparation 5.

Example 8
Capsules Containing Compound 101

101 is dissolved in arachis oil to a final concentration of 1 µg 101/ml oil. 10 Parts by weight of gelatine, 5 parts by weight glycerine, 0.08 parts by weight potassium sorbate, and 14 parts by weight distilled water are mixed together with heating and formed into soft gelatine capsules. These are then filled each with 100 µl of the 101 in oil solution, such that each capsule contains 0.1 µg 101.

Example 9
Dermatological Cream Containing Compound 101

In 1 g almond oil is dissolved 0.05 mg 101. To this solution is added 40 g of mineral oil and 20 g of self-emulsifying beeswax. The mixture is heated to liquify. After the addition of 40 ml hot water, the mixture is mixed well. The resulting cream contains approximately 0.5 µg of 101 per gram of cream.

What we claim is:

1. A compound of the formula I

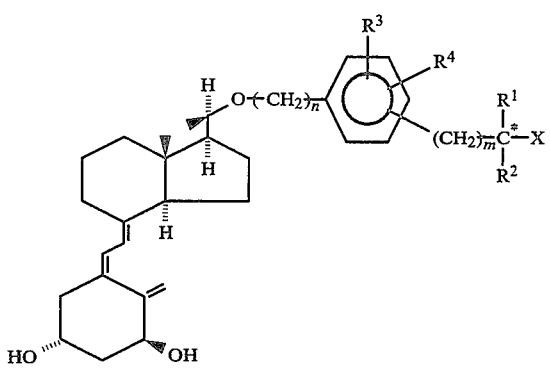

in which $R^1$ and $R^2$ may be the same or different and stand for hydrogen, $C_1$-$C_5$-alkyl, $C_3$-$C_7$-cycloalkyl, or taken together form a $C_3$-$C_8$ carbocyclic ring; X stands for hydrogen or hydroxy, $R^3$ and $R^4$, which may be the same or different stand for hydrogen, $C_1$-$C_5$-alkyl or halogen, n is 0, 1 or 2 and m is 0, 1 or 2; and derivatives of the compounds of formula I in which one or more hydroxy groups have been transformed into —O—acyl or —O—glycosyl or phosphate ester groups, such ester groups being hydrolyzable in vivo.

2. A diastereoisomer of a compound according to claim 1 in pure form or in a mixture of diastereoisomers.

3. A compound according to claim 1, selected from the group consisting of a) 1(S),3(R)-Dihydroxy-20(R)-(3-(2-hydroxy-2-propyl)-phenylmethoxy)-9,10-seco-pregna-5(Z), 7(E),10(19)-triene and b) 1(S),3(R)-Dihydroxy-20(R)-(3-(3-hydroxy-3-pentyl)-phenylmethoxy)-9,10-seco-pregna-5(Z), 7(E),10(19)-triene.

4. A pharmaceutical composition containing a therapeutically effective amount of one or more of the compounds of claim 1, together with pharmaceutically acceptable, non-toxic carriers and/or auxiliary agents.

5. A pharmaceutical composition according to claim 4 in dosage unit form.

6. A dosage unit according to claim 5 containing from 0.1–50 μg of a compound of formula I.

7. A method for producing a compound having formula I

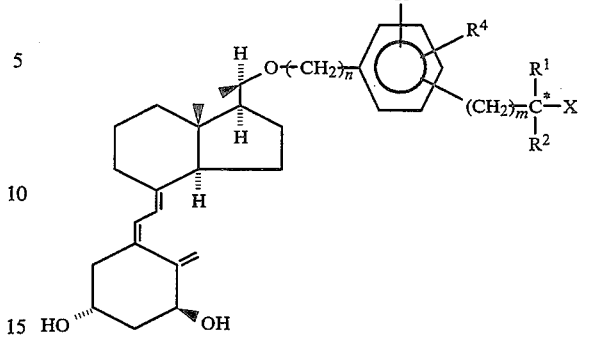

in which $R^1$ and $R^2$ may be the same or different and stand for hydrogen, $C_1$-$C_5$-alkyl, $C_3$-$C_7$-cycloalkyl, or taken together form a $C_3$-$C_8$ carbocyclic ring; X stands for hydrogen or hydroxy, $R^3$ and $R^4$, which may be the same or different stand for hydrogen, $C_1$-$C_5$-alkyl or halogen, n is 0, 1 or 2 and m is 0, 1 or 2; and derivatives of the compounds of formula I in which one or more hydroxy groups have been transformed into —O—acyl or —O—glycosyl or phosphate ester groups, such ester groups being hydrolyzable in vivo comprising, a) alkylating 1(S),3(R)-bis-(tert-butyldimethylsilyloxy)-9,10-seco-pregna-5(E),7(E),10(19)-triene-20(R)-ol under basic conditions with a side chain building block of formula Z-R, in which Z is a leaving group to form a compound of formula III

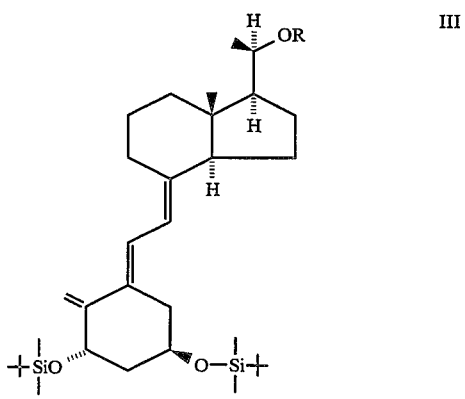

in which

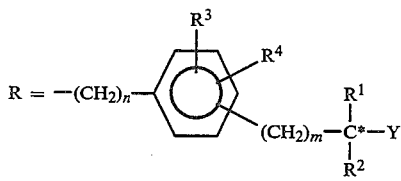

where Y is hydrogen or hydroxyl in which the hydroxyl group may optionally be protected by a protective group and n, m, $R^1$, $R^2$, $R^3$, and $R^4$ are as defined above, b) photoisomerizing under triplet-sensitized conditions a compound of the above formula III and removing protecting groups, if present, to form the desired compound of formula I.

* * * * *